US012678536B2

(12) United States Patent
Noguchi et al.

(10) Patent No.: US 12,678,536 B2
(45) Date of Patent: Jul. 14, 2026

(54) BIOCOMPATIBLE POLYMER, BIOCOMPATIBLE COMPOSITIONS, SOL OR GEL, AND INJECTABLE COMPOSITION

(71) Applicant: KYOCERA CORPORATION, Kyoto (JP)

(72) Inventors: Aya Noguchi, Kyoto (JP); Shihori Yamane, Kyoto (JP); Masayuki Kyomoto, Ritto (JP)

(73) Assignee: KYOCERA Corporation, Kyoto (JP)

( * ) Notice: Subject to any disclaimer, the term of this patent is extended or adjusted under 35 U.S.C. 154(b) by 633 days.

(21) Appl. No.: 18/022,724

(22) PCT Filed: Aug. 26, 2021

(86) PCT No.: PCT/JP2021/031279
§ 371 (c)(1),
(2) Date: Feb. 22, 2023

(87) PCT Pub. No.: WO2022/045230
PCT Pub. Date: Mar. 3, 2022

(65) Prior Publication Data
US 2024/0382649 A1 Nov. 21, 2024

(30) Foreign Application Priority Data
Aug. 27, 2020 (JP) ................................ 2020-143866

(51) Int. Cl.
*A61L 27/20* (2006.01)
*A61L 27/52* (2006.01)
(Continued)

(52) U.S. Cl.
CPC ............... *A61L 27/20* (2013.01); *A61L 27/52* (2013.01); *A61L 27/56* (2013.01); *A61L 27/58* (2013.01);
(Continued)

(58) Field of Classification Search
CPC ...................................................... A61L 27/20
See application file for complete search history.

(56) References Cited

U.S. PATENT DOCUMENTS

2010/0015102 A1 1/2010 Iwasaki
2012/0156164 A1 6/2012 Park
(Continued)

FOREIGN PATENT DOCUMENTS

CN 108853597 * 11/2018
CN 108853597 A 11/2018
(Continued)

OTHER PUBLICATIONS

Liu et al, Glycol Chitosan/Hyaluronic Acids Hydrogel Cartilage Extracellular Matric Particles, Artificial Cells, Nanomedicine and Biotechnology, vol. 46, No. 51, pp. 5721-5732. (Year: 2018).*
(Continued)

*Primary Examiner* — Carlos A Azpuru
(74) *Attorney, Agent, or Firm* — Procopio, Cory, Hargreaves & Savitch LLP

(57) ABSTRACT

Provided is a biocompatible composition or the like that assists cells in the repair of a damaged tissue in a joint cavity. The biocompatible composition or the like according to the disclosure includes a biocompatible polymer having a substituent that adheres or binds to cells and/or a soft tissue in a joint cavity.

15 Claims, 6 Drawing Sheets

(51) Int. Cl.
*A61L 27/56* (2006.01)
*A61L 27/58* (2006.01)

(52) U.S. Cl.
CPC ....... *A61L 2400/06* (2013.01); *A61L 2430/24* (2013.01)

(56) References Cited

U.S. PATENT DOCUMENTS

| | | | |
|---|---|---|---|
| 2013/0189231 | A1 | 7/2013 | Iwasaki |
| 2020/0230288 | A1 | 7/2020 | Cho |

FOREIGN PATENT DOCUMENTS

| | | | | |
|---|---|---|---|---|
| JP | 2013-503688 | | * | 2/2013 |
| JP | 2013-503688 | A | | 2/2013 |
| JP | 2020-506273 | A | | 2/2020 |
| WO | 2008/102855 | A1 | | 8/2008 |

OTHER PUBLICATIONS

Shin. J et al. Tissue Adhesive Catechol-Modified Hyaluronic Acid Hydrogel for Effective. Minimally invasive Cell Therapy. Advanced Functional Materials., 2015, vol. 25, pp. 3814-3824.

Liu, Chun et al. Glycol chitosan/oxidized hyaluronic acid hydrogels functionalized with cartilage extracellular matrix particles and incorporating BMSCs for cartilage repair. Artificial Cells, Nanomedicine, and Biotechnology., 2018, vol. 46, sup. 1, pp. S721-S732, 13 pages.

Pornpitchanarong. Chaiyakarn et al. Catechol-modified chitosan/hyaluronic acid nanoparticles as a new avenue for local delivery of doxorubicin to oral cancer cells. Colloids and Surfaces, B: Biointerfaces., Aug. 1, 2020, vol. 196, Article No. 111279, pp. 1-8.

Igarashi et. al., Repair of articular cartilage defects with a novel injectable in situ forming material in a canine model, Journal of Biomedical Materials Research A, vol. 100A, p. 180-187, 2012.

Ozeki et. al. Not single but periodic injections of synovial mesenchymal stem cells maintain viable cells in knees and inhibit osteoarthritis progression in rats, Osteoarthritis and Cartilage, vol. 24, p. 1061-1070, 2016.

* cited by examiner

BIOCOMPATIBLE POLYMER, BIOCOMPATIBLE COMPOSITIONS, SOL OR GEL, AND INJECTABLE COMPOSITION

TECHNICAL FIELD

The disclosure relates to a biocompatible polymer, a biocompatible composition, a sol or gel, and an injectable composition.

BACKGROUND OF INVENTION

Cell therapy, which is a type of regenerative medicine, is attracting attention as a treatment for issues such as knee osteoarthritis (KOA). Among these cell therapies, treatment methods involving injection of platelet-rich plasma (PRP) or mesenchymal stem cells (MSC) into a joint cavity are less invasive to patients than treatments that require surgery.

Patent Document 1 indicates that bone marrow mesenchymal stem cells are embedded in a composition for cartilage regeneration containing a monovalent metal salt of a low endotoxin alginic acid. Non-Patent Document 1 also reports research using alginates.

Non-Patent Document 2 reports results of a case in which synovial mesenchymal stem cells were injected once or repeatedly into a rat osteoarthritis model.

CITATION LIST

Patent Literature

Patent Document 1: WO 2008/102855

Non-Patent Literature

Non-Patent Document 1: Igarashi et. al., Journal of Biomedical Materials Research A, Vol. 100A, pp. 180-187, 2012

Non-Patent Document 2: Ozeki et. al., Osteoarthritis and Cartilage, Vol. 24, pp. 1061-1070, 2016

SUMMARY

In an aspect of the disclosure, a biocompatible composition includes:

a biocompatible polymer having a substituent that adheres or binds to cells, and/or a soft tissue in a joint cavity.

The biocompatible composition has a mesh structure.

In an aspect of the disclosure, a sol or gel includes:

a biocompatible polymer having a substituent that adheres or binds to cells, and/or a soft tissue within a joint cavity; and a dispersion medium.

In an aspect of the disclosure, a biocompatible polymer has a substituent that adheres or binds to cells, and/or a soft tissue in a joint cavity.

DESCRIPTION OF EMBODIMENTS

An embodiment of the disclosure will be described in detail below. Unless otherwise specified in the present description, "A to B" representing a numerical value range means "A or more and B or less".

1. Biocompatible Polymer

Figure 1:
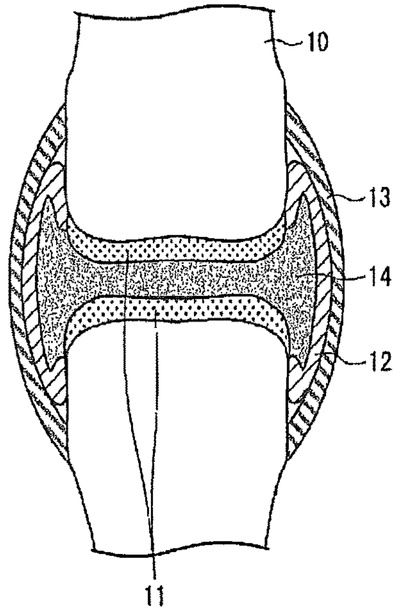
FIG. 1 is a schematic view illustrating a structure of a joint.

First, referring to FIG. 1, an overview of a joint in which a biocompatible polymer according to the disclosure may be applied is described. FIG. 1 is a schematic view illustrating a structure of a joint. Although not illustrated, two bones 10 facing each other in the joint are connected by a ligament. Articular cartilage 11 is present at facing end portions of the two coupled bones 10. The joint is covered by a joint capsule 13. A synovial membrane 12 is present inside the joint capsule 13. The region surrounded by the articular cartilage 11 and the synovial membrane 12 is referred to as a joint cavity 14. The joint cavity 14 is filled with a joint fluid (synovial fluid). In the case of a knee joint, a meniscus is present between the opposing articular cartilages 11.

In an embodiment of the disclosure, a biocompatible polymer has a substituent that adheres or binds to cells and/or a soft tissue (a soft tissue such as articular cartilage and a synovial membrane) in a joint cavity. If the biocompatible polymer has a substituent that adheres to cells, and the biocompatible polymer and cells are injected into a joint cavity, the biocompatible polymer adheres to the cells, and the cells can be contained within the joint cavity. Thus, cellular metabolism and the diffusion of cells outside of the joint cavity can be reduced. If the biocompatible polymer has a substituent that binds to a soft tissue in a joint cavity, the biocompatible polymer covers a soft tissue in a joint cavity, and thereby can reduce cellular metabolism and/or the diffusion of cells outside of the joint cavity.

The biocompatible polymer can be biodegradable or bioabsorbable. Thus, the period during which cells are contacting a soft tissue in a joint cavity can be controlled with decomposition or absorption of the biocompatible polymer in vivo. For example, the biocompatible polymer is decomposed by hydrolysis or enzymes within the body.

Examples of monomer units contained in the main backbone of the biocompatible polymer include glucosamine, β-D-mannuronic acid, α-L-gluronic acid, N-acetyl glucosamine, D-glucuronic acid, N-acetylgalactosamine, β-glucose, ethylene glycol, acrylic acid, caprolactone, lactic acid, glycolic acid, and various amino acids. The biocompatible polymer may be a homopolymer, or may be a copolymer. The main backbone of the biocompatible polymer may include, for example, chitosan, chitin, alginic acid, hyaluronic acid, chondroitin sulfate, gelatin, collagen, cellulose, polyethylene glycol, polyacrylic acid, polycaprolactone, polylactic acid, polyglycolic acid and/or poly(lactic acid-glycolic acid).

The biocompatible polymer may include a mucopolysaccharide as the main backbone. Examples of the mucopolysaccharide include chitosan, chitin, hyaluronic acid, and chondroitin sulfate. Chitosan is a homopolymer containing glucosamine as a monomer unit. Chitin contains N-acetyl glucosamine as a monomer unit, and may contain glucosamine. Hyaluronic acid is a copolymer containing D-glucuronic acid and N-acetyl glucosamine as monomer units. Chondroitin sulfate is a copolymer in which D-glucuronic acid and N-acetyl galactosamine are contained as monomer units, and to which sulfuric acid is bonded. The biocompatible polymer may have a chitosan backbone and/or a hyaluronic acid backbone.

The biocompatible polymer may contain a plurality of types of monomer units having different in vivo decomposition rates. Thus, the biocompatible polymer gradually undergoes in vivo decomposition, and therefore the period during which cells are contacting a soft tissue in a joint cavity can be controlled.

The biocompatible polymer may include a first backbone and a second backbone having a slower decomposition rate than that of the first backbone. Examples of the backbone having a faster decomposition rate include a hyaluronic acid backbone, an alginic acid backbone, and a chondroitin sulfate backbone. Examples of the backbone having a slower decomposition rate include a chitosan backbone and a cellulose backbone. The biocompatible polymer may include a chitosan backbone and a hyaluronic acid backbone. The chitosan backbone has a slower decomposition rate than the hyaluronic acid backbone.

The biocompatible polymer may include a crosslinked structure in which the first backbone and the second backbone are crosslinked by a hydrolyzable functional group. For example, the biocompatible polymer may include a crosslinked structure in which a chitosan backbone and a hyaluronic acid backbone are crosslinked by a hydrolyzable functional group. Specifically, the biocompatible polymer may include a crosslinked structure in which a chitosan backbone and a hyaluronic acid backbone are crosslinked by a Schiff base. The Schiff base includes a carbon-nitrogen double bond. Here, the hyaluronic acid backbone may be formed into an aldehyde in order to bind to an amino group of the chitosan backbone.

In the present description, "adheres or binds to cells and/or a soft tissue in a joint cavity" means that an attractive interaction is exerted with cells and/or a soft tissue in a joint cavity. Examples of the attractive interaction include electrostatic interaction, hydrogen bonding, hydrophobic interaction, ionic bonding, and covalent bonding.

The adhesion surface area ratio of the biocompatible polymer having a substituent that adheres or binds to cells and/or a soft tissue in a joint cavity may be 50% or more, may be 60% or more, or may be 70% or more, as evaluated by a method described in Examples below.

Examples of cells include cells that can engraft to a soft tissue in a joint cavity and repair a damage of the soft tissue within the joint cavity. Examples of such cells include cells used in regenerative medicine such as stem cells and blood cells. Examples of stem cells include mesenchymal stem cells (MSC), induced pluripotent stem cells (iPS cells), and embryonic stem cells (ES cells). Examples of blood cells include platelets and white blood cells. Alternatively, cells may be differentiated chondrocytes, osteoblasts, and the like. Examples of soft tissues in a joint cavity include articular cartilage, synovial membranes, ligaments, and the meniscus.

Examples of the substituent that adheres or binds to cells and/or a soft tissue in a joint cavity include a hydroxyl group-modified aryl group or cell adhesion protein derivatives. Examples of the aryl group of the hydroxyl group-modified aryl group may include a phenyl group, a naphthyl group, and a phenanthryl group. Specific examples of the substituent that adheres or binds to cells or a soft tissue in a joint cavity include a 4-hydroxyphenyl group, a 3,4-dihydroxyphenyl group, a 3,4,5-trihydroxyphenyl group, a fibronectin derivative, a laminin derivative, a lubrysin derivative, a mucin derivative, a cadherin derivative, and an integrin derivative. In addition, the wording "having a substituent that adheres or binds to cells and/or a soft tissue in a joint cavity" in the present description is also meant to encompass an aspect in which attractive interaction is exerted between cell adhesion molecules and the main backbone of the biocompatible polymer. Examples of the attractive interaction include electrostatic interaction, hydrogen bonding, hydrophobic interaction, ionic bonding, and covalent bonding. Examples of the cell adhesion molecule include fibronectin, laminin, lubrysin, mucin, cadherin, and integrin.

The biocompatible polymer may have a substituent that adheres to cells and a substituent that binds to a soft tissue in a joint cavity. Thus, the biocompatible polymer can bind to a soft tissue in a joint cavity and adhere to cells. Thus, through the biocompatible polymer, cells can be retained on a soft tissue in a joint cavity. For example, if the biocompatible polymer has a chain structure, the biocompatible polymer may have a substituent that adheres to cells at a first end and have a substituent that binds to a soft tissue in a joint cavity at a second end separate from the first end. The substituent that adheres to cells and the substituent that binds to a soft tissue in a joint cavity may be the same or different.

A cell migration factor may be bonded to the biocompatible polymer. This can induce the engraftment of cells to a soft tissue in a joint cavity. Examples of the cell migration factor include factors that induce chemotaxis or haptotaxis. Examples of such cell migration factors include RANTES (Regulated on activation, normal T expressed and secreted), MCP-1 (Monocyte chemoattractant protein-1), MIP-3β (Monocyte inflammatory protein-3β), SDF-1α (Stomal cell-derived-factor-1α), BCA-1 (B cell attracting chemokine-1), CXCL16 (Chemokine C-X-C motif ligand 16), EGF (Endothelial growth factor), b-FGF (basic Fibroblast Growth Factor), HGF (Hepatocyte growth factor), TGF-β1 (Transforming growth factor beta 1), IGF-1 (Insulin-like growth factor 1), PDGF-AB (Platelet Derived Growth Factor AB), TNF-α (Tumor necrosis factor-α), collagen, and fibronectin. As described above, collagen can also be the main backbone of the biocompatible polymer. Fibronectin is also a cell-binding molecule as described above.

The biocompatible polymer may have a substituent that improves solubility in a neutral solution. A neutral solution can be, for example, a solvent or dispersion medium described below. Thus, the biocompatible polymer can be easily dissolved in a solvent or dispersion medium. As a result, the biocompatible polymer can be easily injected into a living body. Examples of substituent groups that improve solubility in a neutral solution include a succinyl group, a 4-hydroxyphenyl group, 3,4-dihydroxyphenyl group, 3,4,5-trihydroxyphenyl group, and polyethylene glycol. Of these, the 4-hydroxyphenyl group, the 3,4-dihydroxyphenyl group, and the 3,4,5-trihydroxyphenyl group can be said to have both a property of adhering or bonding to cells and/or a soft tissue in a joint cavity and a property of improving solubility in a neutral solution. The pH of the neutral range may be from 5.5 to 8.5, and in particular, may be from 7.0 to 8.5.

The biocompatible polymer may have a substituent that reduces cellular adhesion and a substituent that binds to a soft tissue in a joint cavity. Thus, the biocompatible polymer can reduce cellular adhesion while binding to a soft tissue in a joint cavity. Thus, cells can be absorbed into a soft tissue within a joint cavity to reduce diffusion outside of the joint cavity. Examples of substituents that reduce cellular adhesion include zwitterionic functional groups. Examples of zwitterionic functional groups include phosphorylcholine groups, sulfobetaine groups, and carboxybetaine groups. A phosphorylcholine group is a group having a quaternary ammonium group and a phosphodiester bond. A sulphobetaine group is a group having a quaternary ammonium group and $—SO_3^-$. A carboxybetaine group is a group having a quaternary ammonium group and $—CH_3COO^-$.

An example of a method for introducing, into the biocompatible polymer, a substituent that adheres or binds to cells and/or a soft tissue in a joint cavity, a substituent that improves solubility in a neutral solution, and/or a substituent that reduces cellular adhesion includes introduction through a dehydration condensation reaction. An example of a method for bonding a cell migration factor to the biocompatible polymer includes a dehydration condensation reaction.

2. Biocompatible Composition

In one embodiment of the disclosure, a biocompatible composition includes the above-described biocompatible polymer having a substituent that adheres or binds to cells and/or a soft tissue in a joint cavity. The biocompatible composition is provided with a mesh structure and/or a microcapsule structure. In other words, the biocompatible polymer forms a mesh structure and/or a microcapsule structure in the biocompatible composition. Thus, the biocompatible composition can contain cells, and therefore the movement of cells to outside of the biocompatible composition is limited. Thus, cellular metabolism and/or the diffusion of cells to outside of a joint cavity can be reduced. If the biocompatible polymer has a substituent that binds to a soft tissue in a joint cavity, the biocompatible composition covers a soft tissue in the joint cavity even without containing of cells, and thereby the biocompatible composition can reduce cellular metabolism and/or the diffusion of cells outside of the joint cavity. As the biocompatible polymer is decomposed, cells engrafts to a soft tissue in the joint cavity.

In the present description, "mesh structure" refers to a structure of a mesh shape formed by bonding of the biocompatible polymer through crosslinking or the like. Also, the "microcapsule structure" means a structure having internally a cavity that is covered by a membrane formed by the biocompatible polymer. The outer diameter of the microcapsule structure may be from 1 to 1000 μm.

The biocompatible composition may include both a mesh structure and a microcapsule structure. For example, the biocompatible composition may contain a mixture of a mesh-shaped structure and a microcapsule-shaped structure. A microcapsule structure may be formed by the mesh structure.

The biocompatible composition may include a mesh structure and/or a microcapsule structure ex vivo, or may include the structures thereof in vivo. For example, a biocompatible composition may be such that a mesh structure and a microcapsule structure are not provided ex vivo, but after the biocompatible composition is injected in vivo, the biocompatible composition may form a mesh structure and/or a microcapsule structure.

The mesh structure and the microcapsule structure may be formed by crosslinking the biocompatible polymer. The crosslinking may be a physical crosslinking by non-covalent bonds, or may be a chemical crosslinking through covalent bonds. The crosslinking site may be a terminal of the biocompatible polymer, or may be a side chain. Crosslinking may be implemented through a crosslinking agent. That is, the biocompatible composition may include a crosslinking agent. Examples of the crosslinking agent include a divalent or higher metal ion, methylene bisacrylamide, ethylene glycol dimethacrylate, and a methylene bisacrylamide derivative. Examples of methods for initiating crosslinking include two-part mixing, a temperature response, and a light response. The biocompatible polymer may be crosslinked by a hydrolyzable functional group as described above.

For example, the mesh structure may be formed by adding a solution containing a crosslinking agent to a solution containing the biocompatible polymer. Alternatively, the microcapsule structure may be formed by dripping or injecting droplets of the biocompatible polymer into a solution containing a crosslinking agent. The microcapsule structure may be formed by dispersing cells into a solution containing a biocompatible polymer having a substituent that adheres to cells, and then stirring the mixture.

Figure 2:
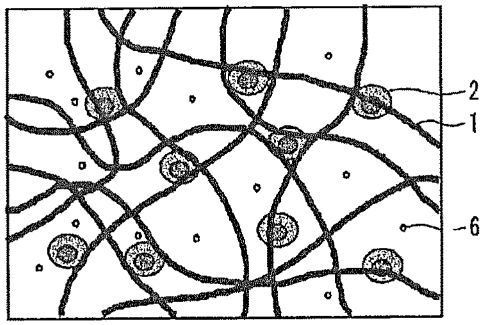
FIG. 2 is a schematic view illustrating a mesh structure formed by a biocompatible polymer according to an embodiment.

FIG. 2 is a schematic view illustrating a mesh structure formed by a biocompatible polymer according to an embodiment. In FIG. 2, cells 2 and bioactive molecules 6 are present in a mesh structure formed by the biocompatible polymer 1. The size (pore diameter) of a mesh in the mesh structure is not particularly limited, but may be 30 μm or less on a surface of the mesh structure, and may be 10 μm or less inside the mesh structure. Cells are more easily retained as the size of the mesh becomes smaller. If the size of the mesh is 1 μm or less, passage of cells to outside of the mesh structure can be further reduced. Alternatively, if the size of the mesh is greater than 1 μm, cells are easily passed through the mesh structure. If the size of the mesh is from 1 to 100 nm, the bioactive molecules 6 are passed through the mesh. Examples of the bioactive molecule 6 include interleukin-10 (IL-10), transforming growth factor-β (TGF β-1), hepatocyte growth factor (HGF), prostaglandin E2 (PGE2), vascular endothelial growth factor (VEGF), basic fibroblast growth factor (bFGF), and tumor necrosis factor (TNFα).

Figure 3:
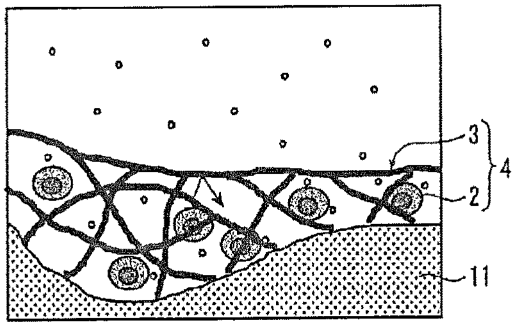
FIG. 3 is a schematic view illustrating a biocompatible composition and complex according to an embodiment.
Figure 4:
FIG. 4 is a schematic view illustrating a biocompatible composition and complex according to an embodiment.

If the biocompatible polymer has a substituent that binds to a soft tissue in a joint cavity, the biocompatible composition can remain on a soft tissue within a joint cavity. Cells can also be retained in the biocompatible composition. For example, if the biocompatible polymer has a substituent that binds with an articular cartilage, as illustrated in FIG. 3, the biocompatible composition 3 containing cells 2 can remain on an articular cartilage 11. If the biocompatible polymer has a substituent that binds to a synovial membrane, as illustrated in FIG. 4, the biocompatible composition 3 containing cells 2 can remain on a synovial membrane 12.

Figure 5:
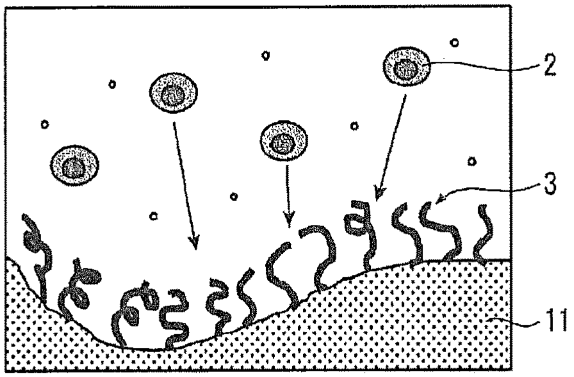
FIG. 5 is a schematic view illustrating a biocompatible composition according to an embodiment.

If the biocompatible polymer has a substituent that adheres to cells and a substituent that binds to a soft tissue in a joint cavity, the diffusion of cells can be further reduced. In this case, even if cells are not contained within the biocompatible composition, the cells can be brought closer to a soft tissue in a joint cavity via the biocompatible composition. For example, as illustrated in FIG. 5, cells 2 can be adhered to the biocompatible compositions 3 bonded on an articular cartilage 11.

Figure 6:
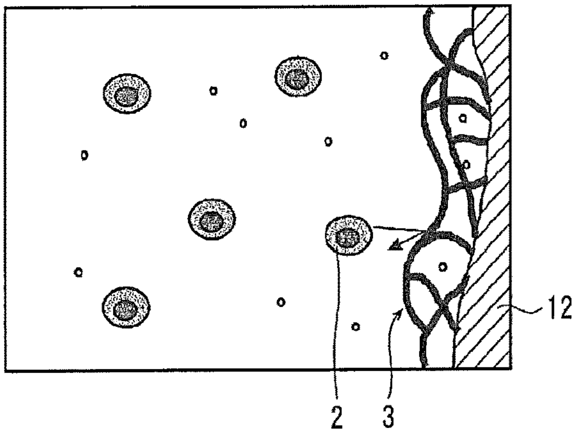
FIG. 6 is a schematic view illustrating a biocompatible composition according to an embodiment.

If the biocompatible polymer has a substituent that reduces cellular adhesion and a substituent that binds to a soft tissue in a joint cavity, the absorption and metabolism of cells by a soft tissue in a joint cavity can be reduced. When the size of the mesh of the mesh structure formed by the biocompatible molecules is less than or equal to 1 μm, and the biocompatible molecule has a substituent that binds to a soft tissue in a joint cavity, diffusion of cells to outside of a joint cavity can be reduced. For example, if the biocompatible polymer contained in the biocompatible composition 3 bonded on a synovial membrane 12 as illustrated in FIG. 6 has a substituent that reduces cellular adhesion, absorption of the cells 2 in capillaries and lymph ducts present in the synovial membrane 12 can be reduced.

Figure 7:
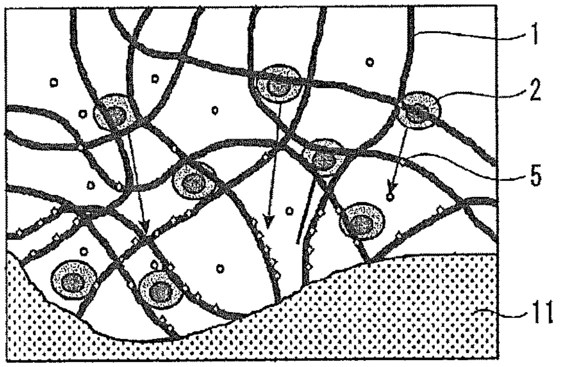
FIG. 7 is a schematic view illustrating a mesh structure formed by a biocompatible polymer according to an embodiment.

When cellular migration factors are bonded to the biocompatible polymer, engraftment of cells to a soft tissue in a joint cavity can be induced. For example, if the biocompatible polymer 1 to which cell migration factors 5 are bonded forms a mesh structure on an articular cartilage 11 as illustrated in FIG. 7, engraftment of cells 2 to the articular cartilage 11 can be induced.

A concentration gradient of cell migration factors may be present in the biocompatible composition. For example, in a joint cavity, the concentration of cell migration factors at the side where the biocompatible composition is in contact with a soft tissue in the joint cavity may be high, and the concentration of cell migration factors at the side where the biocompatible composition is not in contact with any soft tissue in the joint cavity may be low. This type of concentration gradient of such cell migration factors can be formed by controlling, in the biocompatible polymer, details such as the position of the substituent that binds to a soft tissue in a joint cavity and the position at which the cell migration factor is bonded.

The biocompatible composition may include a plurality of different types of biocompatible polymers. That is, the biocompatible composition may be a blend of a plurality of different types of biocompatible polymers. For example, a plurality of types of biocompatible polymers may be mutually intertwined to form a multi-mesh structure by crosslinking the plurality of types of biocompatible polymers. Multi-mesh structures are also referred to as interpenetrating polymer network (IPN) structures. The microcapsule structure may also be formed by a multi-mesh structure.

The biocompatible composition may include a plurality of types of biocompatible polymers having different in vivo decomposition rates. In this case, the biocompatible polymers gradually decompose, and therefore the period of contact of cells with a soft tissue in a joint cavity can be controlled. For example, the biocompatible composition may include a plurality of types of biocompatible polymers that include the first and second backbones described above and have different ratios of these backbones. The biocompatible composition may include a first biocompatible polymer having a larger proportion of the first backbone than the second backbone, and a second biocompatible polymer having a larger proportion of the second backbone than the first backbone. In this case, the first biocompatible polymer may be a biocompatible polymer with a fast decomposition rate, and the second biocompatible polymer may be a biocompatible polymer with a slow decomposition rate. For example, the biocompatible composition may include a plurality of types of biocompatible polymers having different ratios of a chitosan backbone and a hyaluronic acid backbone. When the biocompatible polymer includes a plurality of types of monomer units that differ in decomposition rates in vivo, or in other words, when the biocompatible polymer is a copolymer, the period during which cells are contacting a soft tissue in a joint cavity can be controlled.

In a biocompatible composition containing a biocompatible polymer having a fast in vivo decomposition rate and a biocompatible polymer having a slow in vivo decomposition rate, the biocompatible polymer having a fast in vivo decomposition rate may have a substituent that binds to a soft tissue in a joint cavity. In this case, decomposition occurs gradually from the biocompatible polymer that has a fast decomposition rate and is bonded to a soft tissue in a joint cavity, and thereby a coating film or capsule can be formed on the soft tissue in the joint cavity by the biocompatible polymer having a slow decomposition rate.

Figure 8:
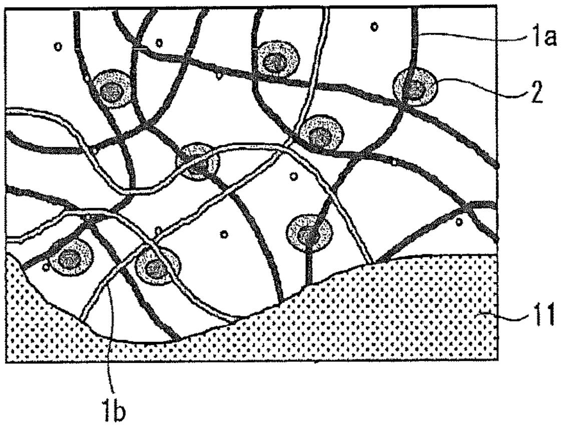
FIG. 8 is a schematic view illustrating a mesh structure formed by a biocompatible polymer according to an embodiment.

For example, as illustrated in FIG. 8, a mesh structure may be formed on an articular cartilage 11 by a biocompatible polymer 1*a* having a slow decomposition rate and a biocompatible polymer 1*b* having a fast decomposition rate. Thus, the size of a mesh in the mesh structure becomes larger as the biocompatible polymer 1*b* having the fast decomposition rate decomposes, and movement of cells 2 is facilitated. Thus, the cells 2 gradually engraft to the articular cartilage 11.

Figure 9:
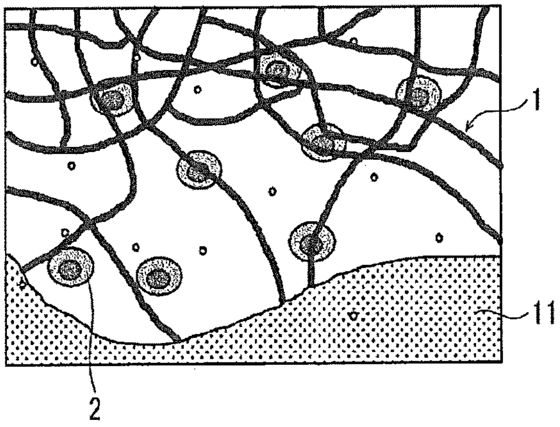
FIG. 9 is a schematic view illustrating a mesh structure formed by a biocompatible polymer according to an embodiment.

The mesh structure may have a gradient in the size of the mesh. For example, in a joint cavity, a mesh may be large at the side where the biocompatible composition is in contact with a soft tissue in the joint cavity, and a mesh may be small at the side where the biocompatible composition is not in contact with any soft tissue in the joint cavity. Through such a mesh size gradient, the diffusion of cells out of the biocompatible composition is reduced, and the movement of cells to near the soft tissue in the joint cavity is facilitated. The mesh size gradient can be formed by controlling, in the biocompatible polymer, details such as the position of the substituent that binds with a soft tissue in a joint cavity, the position of crosslinking, and the concentration of the crosslinking agent in the biocompatible composition. Alternatively, the mesh size gradient can be formed even by using, as described above, a plurality of types of biocompatible polymers having different decomposition rates or a plurality of types of monomer units having different decomposition rates. For example, meshes formed by the biocompatible polymer 1 as in FIG. 9 may have a large size at a side contacting an articular cartilage 11, and may have a small size at a side not contacting the articular cartilage 11.

The biocompatible composition may further include a solvent or a dispersion medium. Examples of the solvent or dispersion medium include water, physiological saline, phosphate buffered saline, a cell culture medium, a culture supernatant, blood, and platelet-rich plasma. A liquid property of the biocompatible composition may be neutral.

The disclosure also encompasses a sol or gel including a biocompatible polymer having a substituent that adheres or binds to cells and/or a soft tissue in a joint cavity, and a dispersion medium. In the present description, "sol" means a composition that has fluidity and contains a biocompatible polymer and a dispersion medium. "Gel" means a composition that has reduced fluidity compared to a sol and contains a biocompatible polymer and a dispersion medium. For example, in a gel, the fluidity may be reduced by forming a mesh structure through crosslinking or the like of the biocompatible polymer as described above. That is, the term "gel" is meant to encompass a biocompatible composition having the mesh structure described above. The term "sol" is meant to encompass a biocompatible composition not having a mesh structure.

Thus, the sol or gel may include the configuration described in the section on the biocompatible composition described above. For example, in a sol or gel, the biocompatible polymer may have a substituent that adheres to cells and a substituent that binds to a soft tissue in a joint cavity. In a sol or gel, cell migration factors may be bonded to the biocompatible polymer. In a sol or gel, the biocompatible polymer may have a substituent that reduces cellular adhesion and a substituent that binds to a soft tissue in a joint cavity. In the sol or gel, the biocompatible polymer may include a plurality of types of monomer units having different in vivo decomposition rates. The sol or gel may include a plurality of types of biocompatible polymers having different in vivo decomposition rates. The sol or gel may contain a plurality of types of the biocompatible polymers having different ratios of a chitosan backbone and a hyaluronic acid backbone. The sol or gel may further include cells.

The dispersion medium may be water, or may be an aqueous solution in which other compounds are dissolved, examples of the aqueous solution including physiological saline, phosphate buffered saline, a cell culture medium, a culture supernatant, blood, and platelet-rich plasma. A liquid property of the sol or gel may be neutral.

The sol may be gelled after being injected into a joint cavity. Thus, injection of the sol can be facilitated. The sol may be immobilized by gelling after reaching a specific site within a joint cavity. For example, by targeting a specific protein present on a surface of a soft tissue in a joint cavity, the sol can reach a specific soft tissue in a joint cavity.

A gradient in the content percentage of the dispersion medium in the gel may be present. For example, in a joint cavity, the content percentage of the dispersion medium may be large at a side where the biocompatible composition is in contact with a soft tissue in the joint cavity, and the content percentage of the dispersion medium may be small at a side where the biocompatible composition is not in contact with any soft tissue in the joint cavity.

3. Complex

In an embodiment of the disclosure, a complex includes a cell and a biocompatible polymer having a substituent that adheres to the cell. The biocompatible polymer adheres to the cell through a substituent that adheres to the cell. According to such complex, the biocompatible polymer is present on the cell, and thereby cell metabolism and/or the diffusion of the cell to outside of the joint cavity can be reduced.

The complex also encompasses an aspect in which cells are included in the biocompatible composition described above. For example, the biocompatible composition 3 containing the cells 2 in FIGS. 3 and 4 may be referred to as a complex 4.

The complex may include the configuration described in the above-described biocompatible composition section. For example, in the complex, the biocompatible polymer may further have a substituent that binds with a soft tissue in a joint cavity. Cell migration factors may be attached to the biocompatible polymer in the complex. In the complex, the biocompatible polymer may include a plurality of types of monomer units having different in vivo decomposition rates. The complex may also include a plurality of types of biocompatible polymers having different in vivo decomposition rates. In the complex, the biocompatible polymer may form a mesh structure. The mesh structure may have a gradient in the size of the mesh.

Figure 10:
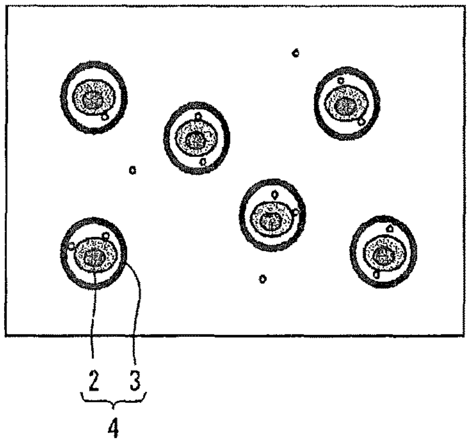
FIG. 10 is a schematic view illustrating a biocompatible composition and a complex according to an embodiment.

Alternatively, the complex may be a microcapsule. The complex may have a structure in which the cells are covered by a film formed by the biocompatible polymer. For example, as illustrated in FIG. 10, the complex 4 may be formed by accommodating a cell 2 within the biocompatible composition 3 having the microcapsule structure described above. It can also be said that in the complex 4, the cell 2 is covered by the biocompatible composition 3 having the microcapsule structure. The microcapsule may allow transmission of a bioactive molecule secreted by the cell accommodated therein to outside of the microcapsule and/or may allow transmission of a bioactive molecule secreted by a cell in a joint cavity to the inside of the microcapsule. The outer diameter of the microcapsule may be from 1 to 1000 μm.

Figure 11:
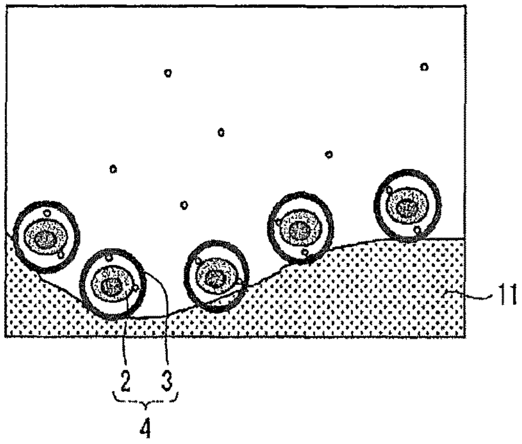
FIG. 11 is a schematic view illustrating a biocompatible composition and a complex according to an embodiment.
Figure 12:
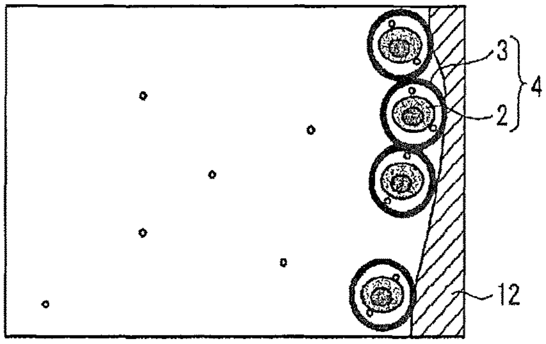
FIG. 12 is a schematic view illustrating a biocompatible composition and a complex according to an embodiment.

A substituent that adheres to cells may be disposed inside the microcapsule. A substituent that binds to a soft tissue in a joint cavity may be disposed at an outer side of the microcapsule. For example, as illustrated in FIG. 11, a complex 4 has a substituent that binds with an articular cartilage 11 and is disposed at an outer side of a microcapsule, and the complex 4 binds to the articular cartilage 11 and thereby improves engraftment of a cell 2 to the articular cartilage 11. As illustrated in FIG. 12, the complex 4 has a substituent that binds to a synovial membrane 12 and is disposed at an outer side of the microcapsule, and the complex 4 binds with the synovial membrane 12 and thereby improves engraftment of a cell 2 to the synovial membrane 12.

In the complex, the biocompatible polymer may be present in some regions on the cell. That is, the entire cell need not be covered by the biocompatible polymer or biocompatible composition. In other words, in the joint cavity, a portion of the surface of the cell contained in the complex may be in contact with the joint fluid. This can reduce the inhibition of secretion of bioactive molecules from the cells. In the complex 4 illustrated in FIG. 13, the biocompatible polymer 1 binds to a surface of a cell 2. As with the complex 4, a biocompatible polymer 1 may be present at multiple locations on the cell 2. For example, a plurality of biocompatible polymers 1 may be bonded to a surface of one cell 2.

Figure 13:
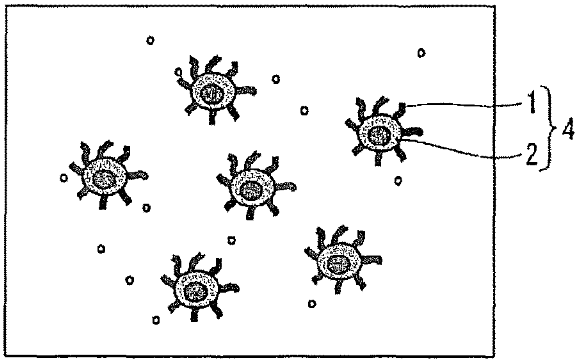
FIG. 13 is a schematic view illustrating a complex according to an embodiment.
Figure 14:
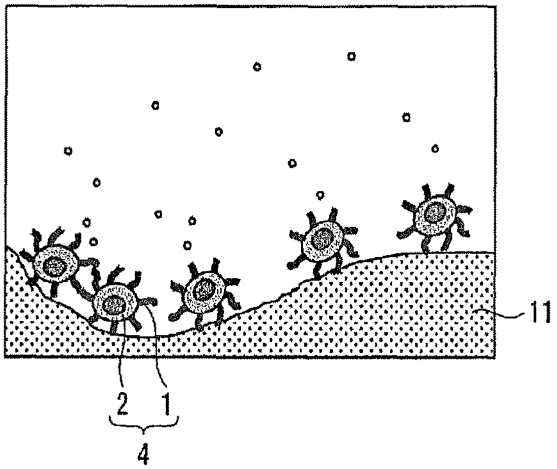
FIG. 14 is a schematic view illustrating a complex according to an embodiment.
Figure 15:
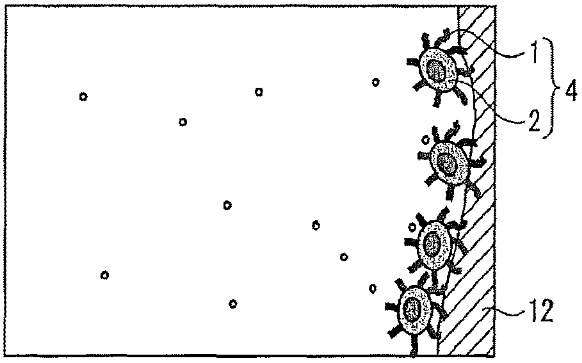
FIG. 15 is a schematic view illustrating a complex according to an embodiment.

In a complex in which biocompatible polymers are present in some regions on the cell, the biocompatible polymer may further have a substituent that binds to a soft tissue within a joint cavity. A substituent that binds to a soft tissue in a joint cavity may be disposed at an end portion separate from the substituent that adheres to a cell in the biocompatible polymer. As illustrated in FIG. 13, if the cell 2 is present inside the complex 4 and the biocompatible polymers 1 surround the area around the cell 2, a substituent that binds to a soft tissue in a joint cavity may be disposed at the outer side of the complex 4. For example, as illustrated in FIG. 14, with the complex 4 having, disposed at an outer side, substituents that bind to an articular cartilage 11, the complex 4 binds to the articular cartilage 11 and thereby improves engraftment of a cell 2 to the articular cartilage 11. As illustrated in FIG. 15, with the complex 4 having, disposed at the outer side, substituents that bind to a synovial membrane 12, the complex 4 binds to the synovial membrane 12 and thereby improves engraftment of the cell 2 to the synovial membrane 12.

Figure 16:
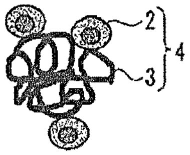
FIG. 16 is a schematic view illustrating a complex according to an embodiment.

The complex may include one cell per complex, or may include a plurality of cells per complex. In the complex 4 illustrated in FIG. 16, a plurality of cells 2 is supported on the biocompatible composition 3.

Figure 17:
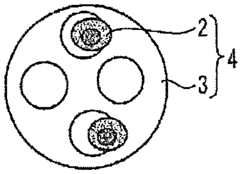
FIG. 17 is a schematic view illustrating a complex according to an embodiment.

The complex may be a porous body. In the complex 4 illustrated in FIG. 17, a carrier having a porous structure is formed by the biocompatible composition 3. Cells 2 are supported in this porous structure. Examples of the method of forming such a porous body include liquid phase methods. The porous body may have the multi-mesh structure described above. The particle size of the porous body may be from 1 to 1000 μm, and the size of the included pore may be from 1 to 50 μm.

4. Suspension

In an embodiment of the disclosure, a suspension includes a complex and a dispersion medium described above. That is, the complex is dispersed in the dispersion medium. This facilitates the injection of cells into a joint cavity. Due to the dispersion of the complex, the suspension may be in the form of a sol or gel. The dispersion medium may be water, or may be an aqueous solution in which other compounds are dissolved, examples of the aqueous solution including physiological saline and phosphate buffered saline.

The suspension may include a plurality of types of complexes having different in vivo decomposition rates. Thus, the complexes gradually undergo in vivo decomposition, and therefore the period during which cells are contacting a soft tissue in a joint cavity can be controlled. Such plurality of types of complexes are produced by using biocompatible polymers containing a plurality of types of monomer units having different in vivo decomposition rates, and/or a plurality of types of biocompatible polymers having different in vivo decomposition rates as described above.

The suspension may include a complex that is a plurality of microcapsules having different particle sizes. This allows a soft tissue in a joint cavity to be densely covered by the complex.

5. Injectable Composition

In an embodiment of the disclosure, an injectable composition includes the above-described biocompatible composition, sol or gel, complex, suspension, or biocompatible polymer. This facilitates the injection of cells into a joint cavity. The injectable composition may include a solvent or dispersion medium described above.

The injectable composition may have a viscosity that enables injection into a joint cavity. For example, the injectable composition may have a viscosity of 1000 mPa·s or less as measured by a cone and plate-type rotary viscometer. Alternatively, when measured with a tuning fork vibrational viscometer, the injectable composition may have a viscosity of 100 mPa·s or less or 50 mPa·s or less.

6. Applications

The above-described biocompatible polymer, biocompatible composition, sol or gel, complex, suspension, or injectable composition (hereinafter, referred to as the biocompatible polymer or the like) may be used to repair a damaged tissue in a joint cavity by cell therapy. Specifically, the biocompatible polymer or the like can be used to transport cells into the joint cavity to aid in the repair of the damaged tissue in the joint cavity. Thus, the biocompatible polymer or the like can be used in the treatment of diseases associated with a soft tissue damage in a joint cavity. Examples of joints having this type of joint cavity include hip joints, knee joints, ankle joints, shoulder joints, elbow joints and finger joints. Alternatively, the joint may be an intervertebral joint including an intervertebral disc.

The disclosure also encompasses a method for treating a disease associated with a soft tissue damage in a joint cavity, the method including a step of injecting the biocompatible polymer or the like into the joint cavity. Examples of diseases associated with a soft tissue damage in a joint cavity include, in addition to knee osteoarthritis, hip osteoarthritis, ankle osteoarthritis, humeral epicondylitis, elbow osteoarthritis, and spondylosis deformans. The joint cavity may be filled with a biocompatible polymer or the like such that the entire joint cavity is filled. Alternatively, a biocompatible polymer or the like may be injected so as to be disposed near a specific tissue.

In the disclosure, the invention was described above based on the various drawings and examples. However, the disclosure is not limited to each embodiment described above. That is, the embodiments of the disclosure can be modified in various ways within the scope illustrated in the disclosure, and embodiments obtained by appropriately combining the technical means disclosed in different embodiments are also included in the technical scope of the disclosure. In other words, note that a person skilled in the art can easily make various variations or modifications based on the disclosure. Note that these variations or modifications are included within the scope of the disclosure.

EXAMPLES

An example of the disclosure will be described below.

Example

Aldehyde hyaluronic acid was dissolved in a 0.5 mol/L MES buffer (pH 4.5) at a concentration of 10 mg/mL and bubbled with Ar gas for 15 minutes. Subsequently, 2.0 mol each of 1-ethyl-3-(3-dimethylaminopropyl) carbodiimide hydrochloride and N-hydroxysuccinimide dopamine hydrochloride were added to the resulting solution, and the mixture was bubbled for 15 minutes. The resulting solution was dialyzed with Milli-Q water having a pH of 4.5, and then lyophilized. Thus, dopamine aldehyde hyaluronic acid into which dopamine was introduced was produced. The dopamine aldehyde hyaluronic acid had a dopamine-derived 3,4-dihydroxyphenyl group as a substituent that adheres or binds to cells and/or a soft tissue in a joint cavity. Hereinafter, the introduced dopamine is also referred to as a "dopamine group". An aqueous solution of dopamine aldehyde hyaluronic acid having a concentration of 20 mg/mL (hyaluronic acid Mw: $3.0\times10^6$, aldehyde group conversion rate: 11%, dopamine group conversion rate: 12%) and an aqueous solution of succinyl chitosan having a concentration of 20 mg/mL (chitosan Mw: $3.55\times10^5$, succinyl group conversion rate: 40%) were mixed at the same volume, and a sample was produced. The biocompatible polymer contained in the sample is represented by Formula (1).

[Chem. 1]

(1)

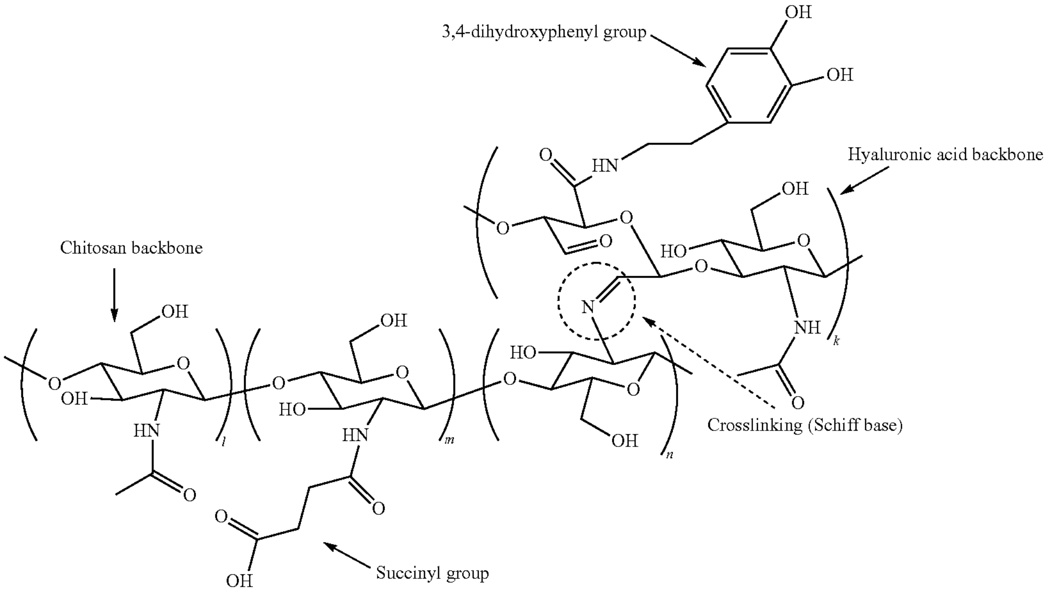

The biocompatible polymer represented by Formula (1) has a hyaluronic acid backbone and a chitosan backbone. The hyaluronic acid backbone and chitosan backbone are crosslinked by a carbon-nitrogen double bond. That is, it can also be said that the hyaluronic acid backbone and the chitosan backbone are crosslinked by a Schiff base. A 3,4-dihydroxyphenyl group derived from dopamine is introduced into the hyaluronic acid backbone. A succinyl group is introduced into the chitosan backbone. k, 1, m, and n represent the number of repeating units. In this example, instead of omitting specific values of the number of repetitions, the weight average molecular weights (Mw) of the hyaluronic acid and chitosan, and the conversion rates of the aldehyde groups, dopamine groups, and succinyl groups are presented as described above.

Comparative Example

An aqueous solution of aldehyde hyaluronic acid having a concentration of 20 mg/mL (hyaluronic acid Mw: $3.0\times10^6$, aldehyde group conversion rate: 11%) and an aqueous solution of succinyl chitosan having a concentration of 20 mg/mL (chitosan Mw: $3.55\times10^5$, succinyl group conversion rate: 40%) were mixed at the same volume, and a sample was produced.

Evaluation Method

Hereinafter, the term "mixing" in "immediately after mixing the sample" and the "mixed sample" means the mixing of the dopamine aldehyde hyaluronic acid aqueous solution or the aldehyde hyaluronic acid aqueous solution, and the succinyl chitosan aqueous solution.

(1) Dynamic Viscoelasticity

Using a dynamic viscoelasticity measurement device (ARES-G2 rheometer, available from TA Instruments Japan Inc.), the storage modulus G' and the loss modulus G" were measured as dynamic viscoelasticity values for 30 minutes immediately after the sample was mixed.

(2) Mesh Structure

The mixed sample was allowed to stand overnight, and was then freeze dried, and an observation sample was produced. An electron microscope image of the sample subjected to Au vapor deposition was produced using a scanning electron microscope (model S-3400, available from Hitachi High-Technologies Corporation) at an acceleration voltage of 15 kV. The pore size was calculated using WinROOF (available from Mitani Corporation).

(3) Viscosity

The viscosity of the mixed sample was measured using a tuning fork vibrational viscometer (model SV-A1, available from A&D Co., Ltd.).

(4) Adhesion of Biocompatible Composition to Tissue Piece

The sample of the Example or Comparative Example was applied to one surface of a tissue piece (chicken skin), and allowed to stand for 5 minutes. Subsequently, the tissue piece coated with the sample of the Example or Comparative Example was stained with Alcian blue, and a microscope image was captured with a digital microscope (model VHX-6000, available from Keyence Corporation). Tissue pieces coated with the sample of the Example or Comparative Example were inserted into a well plate having 12 wells, 0.5 mL of Milli-Q water was added, and the tissue pieces were washed by shaking for 1 hour at 100 rpm. Microscope images of the washed tissue pieces were then captured using a digital microscope. The surface area of the stained portion relative to the tissue piece before and after washing was calculated using ImageJ, and an adhesion surface area ratio of the Example and Comparative Example was calculated by the following equation.

Adhesion surface area ratio (%)=100×(surface area of stained portion of tissue piece after washing)/(surface area of stained portion of tissue piece before washing)

Evaluation Results

Figure 18:
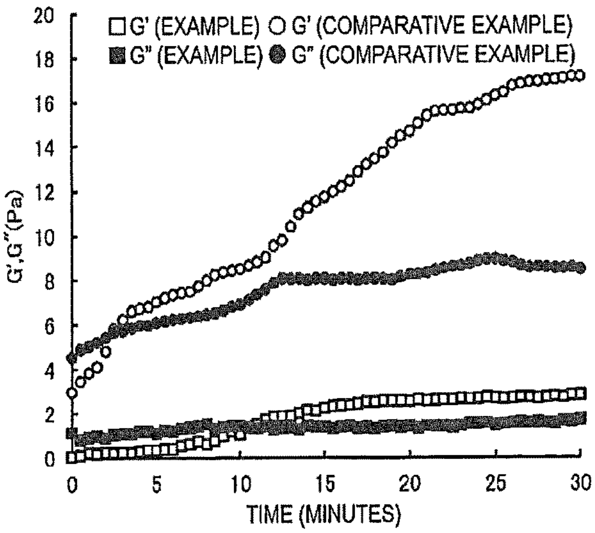
FIG. 18 is a graph showing changes over time in dynamic viscoelasticity in an example and a comparative example.

FIG. 18 is a graph showing changes over time in the dynamic viscoelasticity values G' and G" of the Example and Comparative Example. In both the Example and Comparative Example, G' has points exceeding G", and it is inferred that crosslinking occurred at these points.

Figure 19:
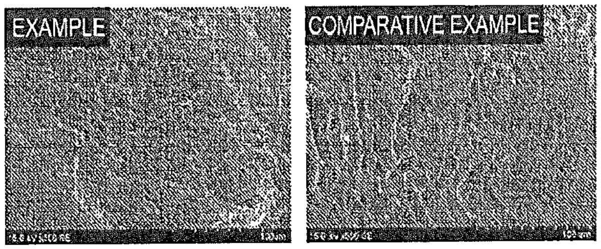
FIG. 19 presents observation views of the example and the comparative example captured by a scanning electron microscope.

FIG. 19 presents observation views of the Example and Comparative Example captured by a scanning electron microscope. Both the Example and Comparative Example have a mesh structure, and it is clear that the Example has a smaller pore size than the Comparative Example. That is, it is found that according to one embodiment of the disclosure, a biocompatible composition having a mesh structure and containing a biocompatible polymer having a substituent that adheres or binds to cells and/or a soft tissue in a joint cavity is produced. Table 1 presents the pore size, viscosity and adhesion surface area ratio of the Example and Comparative Example. While both the Example and Comparative Example have a viscosity that allows injection, it is clear that the viscosity of the Example is reduced more than that of the Comparative Example, and the adhesion surface area ratio of the Example is larger. Thus, the Example can be said to have a viscosity that better facilitates injection. In the Example, an increase in viscosity was expected due to the mutual adhesion of the dopamine, but in practice, the viscosity was reduced. While the viscosity was reduced in the Example, the reduction in pore size and the improvement in adhesive force to tissue pieces was unexpected.

TABLE 1

| | Internal pore size (μm) | Surface pore size (μm) | Viscosity (mPa · s) | Adhesion Surface Area Ratio (%) |
|---|---|---|---|---|
| Example | 6.9 | 23.0 | 23.5 | 75 |
| Comparative Example | 11.6 | 32.6 | 90.6 | 47 |

INDUSTRIAL APPLICABILITY

The disclosure can be used, for example, to repair a damaged soft tissue in a joint cavity.

REFERENCE SIGNS

1 Biocompatible polymer
2 Cell
3 Biocompatible composition
4 Complex
5 Cell migration factor

The invention claimed is:

1. A biocompatible composition comprising:

a mesh structure; and at least one biocompatible polymer, the biocompatible polymer comprising at least one substituent group configured to adhere or bind to either a soft tissue in a joint cavity or a cell, wherein the substituent group configured to adhere or bind to either a soft tissue in a joint cavity or a cell is one or more substituent groups selected from the group consisting of a 4-hydroxyphenyl group, a 3,4-dihydroxyphenyl group, a 3,4,5-trihydroxyphenyl group, and a cell adhesion protein derivative.

2. The biocompatible composition according to claim 1, wherein the at least one biocompatible polymer comprises:

a substituent group that adheres to a cell; and a substituent group that binds to a soft tissue in a joint cavity.

3. The biocompatible composition according to claim 1, wherein the at least one biocompatible polymer comprises a plurality of types of monomer units having different in vivo decomposition rates.

4. The biocompatible composition according to claim 1, wherein, as the at least one biocompatible polymer, a plurality of types of biocompatible polymers having different in vivo decomposition rates is comprised.

5. The biocompatible composition according to claim 1, wherein the at least one biocompatible polymer comprises a substituent group that improves solubility of the biocompatible polymer in a neutral solution.

6. The biocompatible composition according to claim 5, wherein the substituent group that improves the solubility of the biocompatible polymer in a neutral solution is one or more substituents selected from the group consisting of a succinyl group, a 4-hydroxyphenyl group, a 3,4-dihydroxyphenyl group, a 3,4,5-trihydroxyphenyl group, and polyethylene glycol.

7. The biocompatible composition according to claim 1, further comprising a solvent or dispersion medium, wherein a liquid property of the biocompatible composition is neutral.

8. The biocompatible composition according to claim 1, wherein the at least one biocompatible polymer comprises a mucopolysaccharide as a main backbone.

9. The biocompatible composition according to claim 1, wherein the at least one biocompatible polymer comprises a chitosan backbone and/or a hyaluronic acid backbone.

10. The biocompatible composition according to claim 1, wherein the at least one biocompatible polymer comprises a chitosan backbone and a hyaluronic acid backbone.

11. The biocompatible composition according to claim 10, wherein the chitosan backbone and the hyaluronic acid backbone are crosslinked by a hydrolyzable functional group.

12. The biocompatible composition according to claim 10, wherein the chitosan backbone and the hyaluronic acid backbone are crosslinked by a Schiff base.

13. The biocompatible composition according to claim 10, the at least one biocompatible polymer comprising:

a first polymer having a first ratio of the chitosan backbone to the hyaluronic acid backbone; and a second polymer having a second ratio of the chitosan backbone to the hyaluronic acid backbone, the second ratio not equal to the first ratio.

14. The biocompatible composition according to claim 1, wherein the mesh structure has a gradient in a size of a mesh.

15. A sol orgel comprising:

a biocompatible composition described in claim 1; and a dispersion medium.

* * * * *